(12) United States Patent
Gnedenko et al.

(10) Patent No.: US 7,513,371 B2
(45) Date of Patent: Apr. 7, 2009

(54) SYSTEM FOR CONTROLLING THE LEVEL OF POTENTIAL POLLUTANTS IN A WASTE TREATMENT PLANT

(75) Inventors: Valeri G. Gnedenko, Moscow (RU); Igor V. Goryachev, Moscow (RU); Sergei A. Dmitriev, Moscow (RU); David Pegaz, Netanya (IL)

(73) Assignee: E.E.R. Environmental Energy Resources (Israel) Ltd., Ramat-gan (IL)

( * ) Notice: Subject to any disclaimer, the term of this patent is extended or adjusted under 35 U.S.C. 154(b) by 11 days.

(21) Appl. No.: 10/593,869

(22) PCT Filed: Mar. 17, 2005

(86) PCT No.: PCT/IL2005/000310

§ 371 (c)(1), (2), (4) Date: Jul. 30, 2007

(87) PCT Pub. No.: WO2005/090040

PCT Pub. Date: Sep. 29, 2005

(65) Prior Publication Data

US 2008/0006562 A1  Jan. 10, 2008

(30) Foreign Application Priority Data

Mar. 22, 2004  (IL)  .................................. 161011

(51) Int. Cl.
*B07C 5/00* (2006.01)

(52) U.S. Cl. .................... 209/552; 209/592; 250/359.1; 376/163

(58) Field of Classification Search ................. 209/552, 209/592; 250/359.1; 376/163
See application file for complete search history.

(56) References Cited

U.S. PATENT DOCUMENTS 3,794,843 A    2/1974   Chen (Continued)

FOREIGN PATENT DOCUMENTS

DE    2515981 A1    10/1976

(Continued)

OTHER PUBLICATIONS

V.G. Gnedenko et al., "Analysis of Implementation Possibilities of Nuclear-Physical Methods of Determining Elementary Composition of Complex-Composited Materials", Conversion in Machine Building of Russia, Issue No. 1 (62), Jan.-Feb. 2004.

*Primary Examiner*—Patrick H Mackey
*Assistant Examiner*—Terrell H Matthews
(74) *Attorney, Agent, or Firm*—Browdy and Neimark, P.L.L.C.

(57) ABSTRACT

The invention is an apparatus and method for on-line sorting of waste matter, at the entrance to a waste processing plant, according to the level of specific chemicals, typically chlorine detected therein. The apparatus comprises a waste matter inlet that provides waste matter to a weighing module, preferably until a preset limit is reached. Then, this control volume of waste is introduced into a pulsed neutron material analyzer that is optimized for the determination of the content of the specific chemical in the control volume. A control means such as a computer then decides whether the level of the chemical in the waste control volume is above or below a preset threshold, and accordingly channels the waste into one or another of two channels. One of these channels accepts waste with low content of the given chemical, for introduction into the waste processing chamber. The other channel stores the waste until, for example, it may be mixed with other waste having a sufficient low content such that the overall amount of the chemical is still below the threshold value.

20 Claims, 4 Drawing Sheets

U.S. PATENT DOCUMENTS

| | | |
|---|---|---|
| 3,826,789 A | 7/1974 | Yokokawa |
| 4,028,267 A | 6/1977 | Christell et al. |
| 4,582,992 A * | 4/1986 | Atwell et al. ............ 250/359.1 |
| 4,597,487 A * | 7/1986 | Crosby et al. ............... 194/209 |
| 4,702,379 A | 10/1987 | Clayton et al. |
| 4,830,193 A | 5/1989 | Clayton et al. |
| 5,162,095 A * | 11/1992 | Alegre et al. ................ 376/159 |
| 5,472,997 A | 12/1995 | Koslowski et al. |
| 5,948,137 A * | 9/1999 | Pflaum ...................... 75/10.12 |
| 6,233,298 B1 | 5/2001 | Bowman |
| 6,380,503 B1 * | 4/2002 | Mills et al. ................. 209/586 |
| 6,514,631 B1 | 2/2003 | Yamamoto et al. |
| 6,577,697 B2 | 6/2003 | Pearcy et al. |
| 6,880,566 B2 * | 4/2005 | Newman .................... 137/377 |

FOREIGN PATENT DOCUMENTS

| | | |
|---|---|---|
| DE | 4024130 A1 | 2/1992 |
| GB | 1243603 | 8/1971 |
| JP | 6210632 | 8/1994 |
| JP | 10258428 | 9/1998 |
| JP | 2000126649 | 5/2000 |
| JP | 2002137224 | 5/2002 |
| WO | 0031470 | 6/2000 |
| WO | 02074845 A1 | 9/2002 |

* cited by examiner

SYSTEM FOR CONTROLLING THE LEVEL OF POTENTIAL POLLUTANTS IN A WASTE TREATMENT PLANT

FIELD OF THE INVENTION

The present invention relates to an apparatus for sorting of waste according to its chemical composition. In particular, the present invention is directed toward providing a system, comprising the apparatus, which insures that the amount of chlorine containing components introduced into a plant or apparatus for the conversion (including the processing, treatment or disposal) of waste does not exceed a predetermined value.

BACKGROUND OF THE INVENTION

The processing of waste including municipal waste, medical waste, toxic and radioactive waste by means of plasma-torch based waste processing plants is well known.

One problem commonly encountered in the operation of such plants is that of minimizing the production and emission of chlorine containing compounds resulting from the plasma treatment of the waste. Waste, particularly municipal solid waste (MSW), typically comprises a mixture of solid waste which often contains unpredictable levels of chlorine containing materials, for example, PVC pipes, plastic containers, etc. If too large an amount of such materials is processed at any one time in the processing plant, then the level of emission of pollutants containing chlorine may exceed safety and/or legal limits, requiring the plant to be shut down temporarily or alternatively upgrading the gas cleaning system, thus increasing the cost of operation and/or investment of the plant. Further, high levels of chlorine-containing materials may also cause harm to the equipment of the plant, requiring more frequent maintenance operations and may also interfere with the chemical processes that take place during the processing procedure.

Accordingly, it would be advantageous in such plants to monitor the composition of the waste before it is fed into the plant, and to remove from processing, at least temporarily, batches of waste having excessively high chlorine content.

U.S. Pat. No. 3,794,843 relates to a gauge for determining the percentage by weight of moisture contained in a bulk material. U.S. Pat. No. 4,028,267 is directed to an apparatus and method for measuring the concentration of iron in iron ore, by exposing the material to a neutron source. JP 10258428, JP 2002137224, JP 2000126649 and JP 06210632 describe various means for separating or sorting plastics from other material, none of which means makes use of a neutron generator. U.S. Pat. No. 4,702,379 and U.S. Pat. No. 4,830,193, relate to a plant specifically for sorting discrete pieces of gold ore which is irradiated while descending through rotating cylinders in a continuous process.

However, none of these references provides a solution to or in fact even addresses the problems relating to determining the content of chorine-containing materials in waste, particularly for the purpose of removing such waste from subsequent processing in a plasma-torch based processing plant if the amount of chlorine exceeds a predetermined value.

It is therefore an aim of the present invention to provide an apparatus for determining the level of chlorine-containing materials in batches of waste prior to feeding them into a plasma waste converting plant, and a system for separating and processing waste that contains a quantity of chorine-containing material that exceeds a predetermined threshold value.

It is another aim of the present invention to provide such an apparatus and system that may be incorporated into a municipal solid waste processing apparatus.

It is another aim of the present invention to provide such an apparatus and system that is relatively simple mechanically and thus economic to incorporate into a processing plant design.

It is another aim of the present invention to provide such an apparatus and system that is incorporated as an integral part of a plasma-torch based type waste converter.

It is also an aim of the present invention to provide such an apparatus and system that is readily retrofittable with respect to at least some existing plasma-torch based waste converters and other systems for thermal treatment of waste such as incinerators.

Further purposes and advantages of this invention will appear as the description proceeds.

SUMMARY OF THE INVENTION

This invention is directed at a material sorting machine for sorting waste matter according to the level of specific chemicals, typically chlorine detected therein. The machine comprises a waste matter inlet that provides waste matter to a weighing module, preferably until a preset limit is reached. Then, this control volume of waste is introduced into a pulsed neutron material analyzer that is optimized for the determination of chlorine content in the control volume. A control means such as a computer then decides whether the level of chlorine in the waste control volume is above or below a preset threshold, and accordingly channels the waste into one or another of two channels. One of these channels accepts waste with low chlorine content, for introduction into the waste processing chamber. The other channel stores the waste until, for example, it may be mixed with other waste having a sufficient low level of chorine content such that the overall proportion of chlorine is still below the threshold value. The chlorine content is typically in the form of chlorides, particularly PVC.

In a first aspect the present invention provides an apparatus for the sorting of bulk material according to its chemical composition and directing said bulk material into one of two or more channels according to predetermined criterion. The apparatus comprises:

- a loading unit, adapted to accept the bulk material from one or more external sources;
- a weighing unit, adapted for accepting the bulk material from the loading unit in batches and determining the weight of each of the batches;
- a detector module, adapted for accepting a batch of the bulk material from the weighing unit and determining the presence and amount of one or more specified chemical elements in the batch;
- a diverter gate, adapted to accept a batch of material from said detector module and to direct the batch into one of the two or more channels; and
- a controller, adapted to control the activation and the timing of the activation of the elements of the apparatus and to perform calculations and store data necessary for the operation of the apparatus.

The detector module of the apparatus of the invention comprises elements for performing a neutron activation analysis technique to determine the presence and amount of the one or more specified chemical elements in the batch. The results of the determination are used to decide into which of the channels the batch is to be directed.

In preferred embodiments of the apparatus of the invention, the bulk material is waste, which is to be introduced into a waste processing plant or apparatus.

Preferably the predetermined criteria is whether the amount of the specified chemical is less than or greater than a predetermined threshold value. In the preferred embodiments the specified chemical element is chlorine.

In preferred embodiments of the apparatus of the invention, the detector module comprises:
- a neutron moderator casing, made from a suitable hydrogenous material, such as, for example borated polyethylene;
- an upper and a lower opening to the casing that can be selectively opened or sealed by doors;
- an inner chamber whose shape and dimensions are defined by the inner walls of the casing and the upper and lower openings;
- a suitable neutron generator for emitting neutrons to irradiate a batch of bulk material in the inner chamber; and
- a suitable spectrometric gamma detector for detecting gamma quanta.

The emitted neutrons interact with different nuclei within the material thus producing excited nuclei. The excited nuclei decay emitting gamma quanta of different energies that are characteristic of the nuclei and the detector detects the gamma quanta emitted by the nuclei and measures their intensity as a function of their energy.

In a preferred embodiment of the apparatus of the invention, the upper door is pivotally mounted on one end of an arm which has a funnel mounted on its other end, such that, upon rotation of the arm, alternately the upper door either seals the upper opening or the funnel is moved into position to assist in passage of the batches of bulk material from the weighing unit into the inner chamber.

In preferred embodiments of the apparatus of the invention, the neutron generator is a portable D-T pulsed neutron generator; the energy of the emitted neutrons is either 2.5 Mev or 14.0 Mev; the period of time of the pulses are on the order of several seconds, preferably on the order of 10 seconds; and the spectrometric gamma detector is chosen from the group comprising: NaI(Tl) and CsI(Tl)-scintillation detectors.

In another aspect, the invention provides a system for processing waste. The system comprises the sorting apparatus of the invention and further comprises:
- a waste processing plant or apparatus;
- a waste receiving bin, into which waste from a plurality of sources is initially dumped, awaiting transport to the sorting apparatus and eventual processing by the waste processing plant or apparatus; and
- a suitable transport system for transporting waste from the bin to the sorting apparatus and from the sorting apparatus to the waste processing plant or apparatus or to some other location.

The sorting apparatus has three functions: the first function being to divide the waste into substantially equal-volume batches, the second function being to measure the amount of chlorine present in each of the batches, and the third function being to feed each of the batches of waste into one of two channels according to the measured amount of chlorine. The use of the system of the invention insures that the amount of chlorine containing compounds introduced into the plant or apparatus for the conversion of waste does not exceed a predetermined value.

In the preferred embodiment of the system of the invention, wherein, if the amount of chlorine in a batch is below a predetermined threshold, the batch is accepted and diverted to the first of the two channels; wherein the batch of waste is transported to the processing plant, to be processed therein in the normal manner. If the amount of chlorine is above a predetermined threshold, the batch is rejected and diverted to the second of the two channels, to be disposed of in a manner selected from the group comprising the following options:
- option 1, the rejected batches of waste, in the second channel, are stored, and eventually disposed of by not being admitted to the waste processing plant or apparatus;
- option 2, the rejected batches of waste, in the second channel, are placed in temporary storage, and dealt with at a later time;
- option 3, the rejected batches of waste in the second channel are returned to the bin, to be re-mixed with other waste, and sent through the sorting apparatus again.

The rejected batches of waste, according to option 1, can be disposed of at specially designated sites such as municipal solid waste landfills. In a preferred embodiment of the system, each of the rejected batches of waste, according to option 2, is assigned an identification numbed by the control unit, which also contains data regarding the amount of chlorine in each of the batches and the flow rate of waste through the processing plant. Thus, at any given time, the amount of chlorine present in the waste that is being processed by the processing plant is known. Additionally, suitable sensors at the gas outlet of the plant monitor the gaseous chlorine compounds emitted by the plant and provide this data on a real time basis to the controller. Thus the controller can then determine whether at any given time, the level of chlorine containing emission is sufficiently low to permit one or more of the rejected batches in the second channel to be introduced into the plant. In some embodiments the rejected batches of waste, according to option 2, are further sorted or arranged on a turntable type arrangement such that the controller can select, access, and dispatch to the processing plant the particular batch that is the most suitable to maintain the maximum flow rate of chlorine through the plant at any given time. Any one or all of the options 1 to 3 can be operational at any given time, and the controller may switch from one option to another, according to need.

In the preferred embodiments of the system of the invention, the waste processing plant or apparatus process the waste by using a thermal treatment process. The thermal treatment process can comprise the use of one or more plasma torches.

In a further aspect there is provided a method for operating the system of the invention. The method comprises the steps of:
- dumping waste from a plurality of sources into the waste receiving bin;
- transporting at least part of the waste from the waste receiving bin to the loading unit of the sorting apparatus;
- loading at least part of the transported waste into the loading unit;
- transferring at least part of the waste in the loading unit to the weighing unit;
- stopping transfer of waste into the weighing unit when a predetermined amount of waste (referred to as a "batch" of waste) has entered the weighing unit;
- transferring the batch of waste to the detector module;
- sealing the doors of the detector module;
- activating the neutron generator to irradiate the batch of waste in the detector module, thus creating excited nuclei in at least some of the molecules of the material of which the batch of waste is comprised;
- activating the gamma detector to measure the quantity and energy of the gamma quanta emitted by the excited nuclei;

directing the batch through a diverter gate to one of two or more channels; and repeating all of the above steps until no more waste remains in the receiving bin or the processing of the waste must be suspended for some other reason.

The selection of which one of the two or more channels to which the batch is directed is dependent on the results of the measurement of the quantity and energy of the gamma quanta. One of the channels leads directly to the waste processing chamber of the waste processing plant or apparatus. A second of the two or more channels leads to either a temporary storage area, back to the waste receiving bin, or to a disposal area that is not a part of the waste processing plant or apparatus.

In preferred embodiments of the method of the invention, a controller is used to control the activation and the timing of the activation of the elements of the system, to perform calculations, and to store data necessary for the system's operation.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

The term "waste converting apparatus" herein includes any apparatus adapted for thermally treating, processing or disposing of any waste materials, including municipal solid waste (MSW), industrial waste [IW], medical waste [MW], radioactive waste [RW], effluent treatment sludge (ETS), and other types of waste, in particular by means of plasma treatment.

The present invention relates to an apparatus for determining the chemical content of waste to be processed in a plasma torch based processing plant. This apparatus is the principal component of a sorting system that is particularly adapted for ensuring that the amount of chlorine, typically in the form of chlorine containing materials, which is being processed by the plant at any given time, is below a predetermined threshold.

Figure 1:
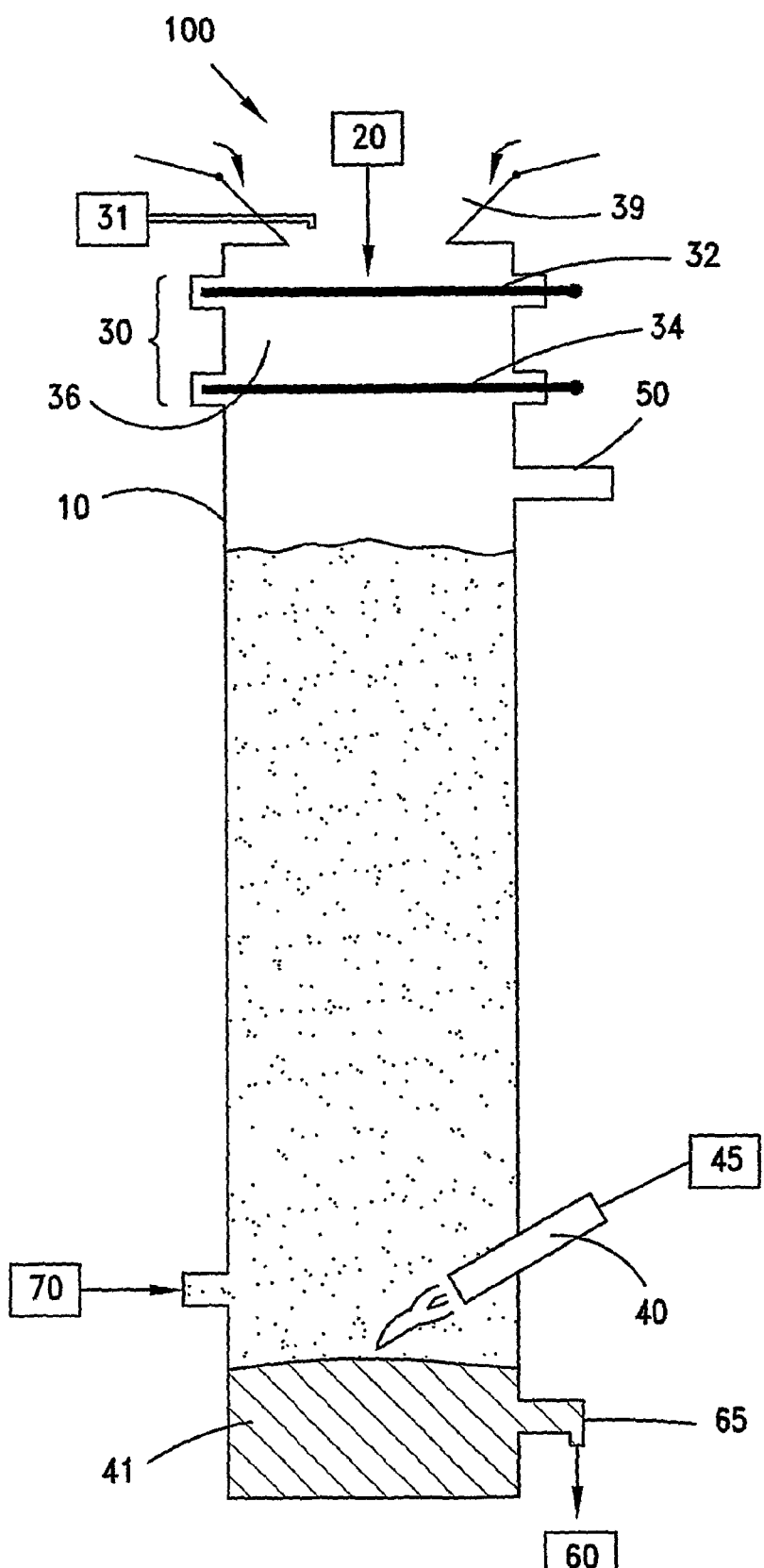
FIG. 1 shows schematically the general layout and main elements of a typical waste plasma processing apparatus of the prior art.

Referring to FIG. 1, a typical plasma waste processing converting apparatus or plant, designated by the numeral (100), comprises a shaft furnace or processing chamber (10). Typically, a solid and/or mixed waste feeding system (20) introduces waste at the upper end of the chamber (10) via a waste inlet means comprising an air lock arrangement (30). The waste feeding system (20) may comprise any suitable conveyor means or the like, and may further comprise a shredder for breaking up the waste into smaller pieces. The air lock arrangement (30) may comprise an upper valve (32) and a lower valve (34) defining a loading chamber (36) there between. The valves (32), (34) are preferably gate valves operated electrically, pneumatically or hydraulically to open and close independently as required. Typically, a closeable hopper arrangement (39) funnels typically solid and/or mixed waste from the feeding system (20) into the loading chamber (36) when the upper valve (32) is open, and the lower valve (34) is in the closed position. Feeding of waste into the loading chamber (36) typically continues until the level of waste in the loading chamber (36) reaches a predetermined point below full capacity, to minimize the possibility of any waste interfering with closure of the upper valve (32). The upper valve (32) is then closed. In the closed position, each of the valves (32), (34) provides an air seal. When required, the lower valve (34) is then opened enabling the waste to be fed into the processing chamber (10) with relatively little or no air being drawn therewith. The opening and closing of the valves (32), (34), and the feeding of waste from the feeder (20) may be controlled by any suitable controller, which may comprise a human controller and/or a suitable computer control system, operatively connected thereto and to other components of the plant (100). Optionally, the hopper arrangement (39) may comprise a disinfectant spraying system (31) for periodically or continuously spraying the same with disinfectant, as required, particularly when medical waste is being processed by plant (100).

The processing chamber (10) also comprises a lower part, having one or a plurality of plasma torches (40) operatively connected to suitable electric power, gas, and water coolant sources (45) and an oxidizer inlet (70). Pyrolysis and gasification take place in the lower part of the processing chamber which also comprises a liquid product collection zone (41) having at least one outlet (65) associated with one or more collection reservoirs (60). The processing chamber (10) further comprises at the upper end thereof at least one gas outlet (50), primarily for channeling away product gases.

The inner facing surfaces of processing chamber (10), at least of the lower part thereof, are typically made from one or more suitable refractory materials, such as for example alumina, alumina-silica, magnesite, chrome-magnesite, chamotte or firebrick. Typically, the processing chamber (10), and generally the plant (100) as a whole, is covered by a metal layer or casing to improve mechanical integrity thereof and to enable the processing chamber to be hermetically sealed with respect to the external environment.

Figure 2:
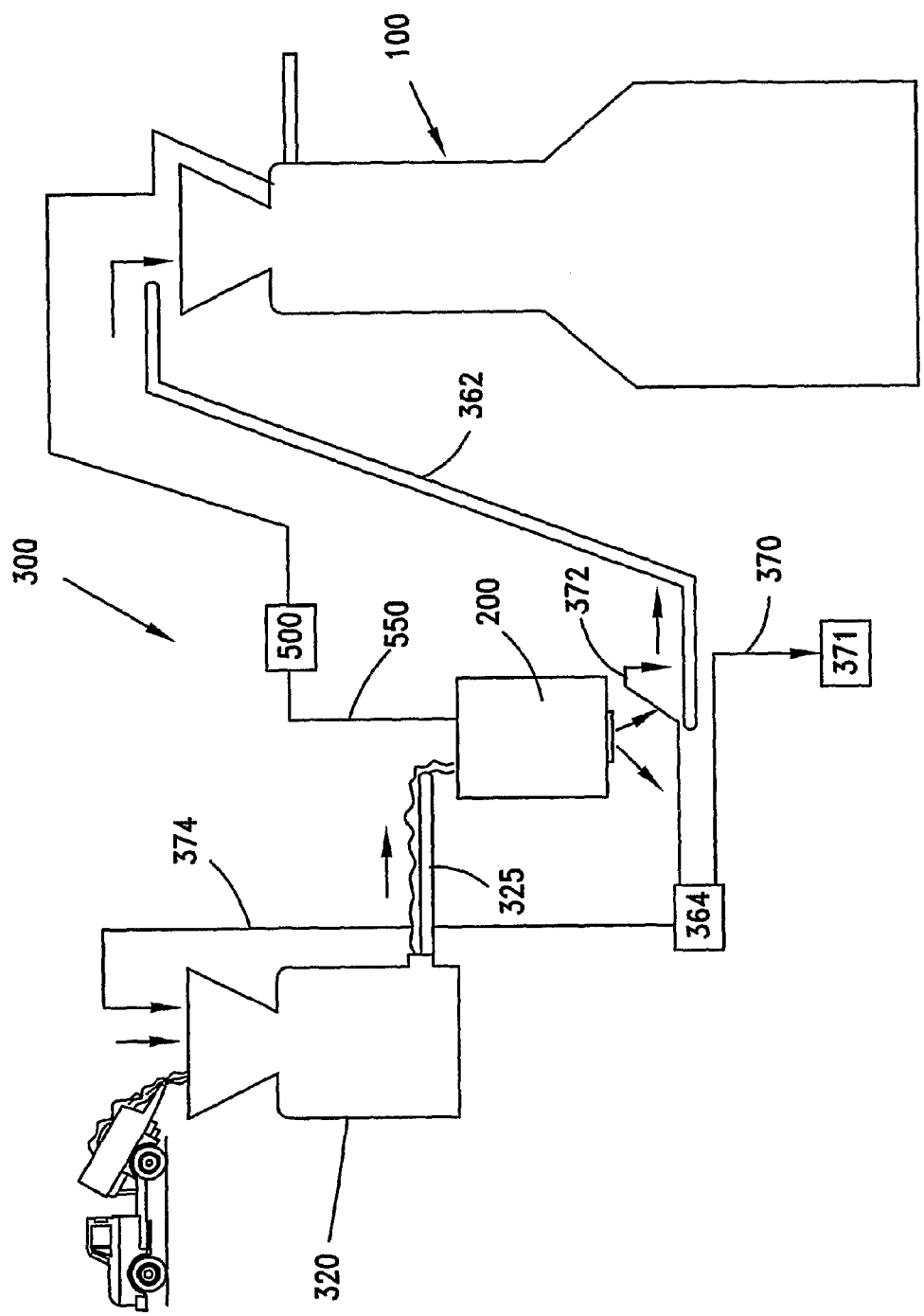
FIG. 2 shows schematically the general layout of a preferred embodiment of the system of the present invention in conjunction with a typical waste plasma processing apparatus.

The present invention is particularly suitable for determining the chemical composition of and sorting waste before it is introduced into such a plant. Referring to FIG. 2, the sorting system according to a preferred embodiment, generally designated by the numeral (300), comprises a waste receiving bin (320), into which waste from a plurality of sources is initially dumped, awaiting sorting and eventual processing by the waste processing plant (100). A suitable transport system (325), for example a conveyor belt or crane, transports waste from the bin (320) to a sorter (200), which will be described in greater detail hereinbelow. Sorter (200) has three functions. The first function is to divide the waste into substantially equal-volume batches, the second function is to measure the amount of chlorine present in each batch, and the third function is to feed each batch of waste, after passing through the sorter (200), into one of two channels according to the measured amount of chlorine. Typically, if the amount of chlorine in a batch is below a predetermined threshold, the batch is accepted and diverted to the first channel (362), and this batch of waste is transported to the processing plant (100), to be processed therein in the normal manner. On the other hand, if the amount of chlorine is above a predetermined threshold, the batch is rejected and diverted to the second channel (364), and a number of options are available for dealing with this batch of waste.

In the first option (370), the rejected waste in the second channel is stored (371), and eventually disposed of by not being admitted to the waste processing plant or apparatus, such that harmful chlorine containing products are not produced. For example, these batches of waste are disposed of at specially designated sites such as municipal solid waste landfills.

In the second option (372), the rejected batches of waste are placed in temporary storage, and dealt with in one of a number of different ways. In a preferred embodiment, for example, each batch is identified by a control unit (500), which also contains data regarding the amount of chlorine in each of the corresponding batches. The data concerning the amount of chlorine is provided by the sorter (200), which is operatively connected to the controller (500) via communication link (550). At any given time, the amount of chlorine present in the waste that is being processed by the processing plant (100) is known from historical data that is available to the controller. The controller (500) is also operatively connected to the processing chamber (10), and determines the flow rate of waste through the chamber (10) by, for example measuring the time interval between consecutive openings of valve 32 or 34. Together with data provided by the sorter (200) regarding the number of batches of waste provided to the plant (100), the amount of chlorine in each batch, and the time interval between any given batch leaving the sorter via the first channel and being introduced into the chamber (10), the controller (500) is able to make a determination of the amount of chlorine being processed at any given time by the plant. Suitable sensors at the gas outlet of the plant (100) monitor the gaseous chlorine compounds emitted by the plant (100), and provide this data on a real time basis to the controller (500). The controller (500) can then determine whether at any given time, the level of chlorine emission is sufficiently low to permit one or more of the rejected batches in the second channel to be introduced into the plant (100). This may happen, for example, when the batches of waste most recently provided via the first channel comprise amounts of chlorine substantially below the threshold. In this option, the rejected batches stored in the second channel (364) may be further sorted or arranged on a turntable type arrangement such that the controller can select, access, and dispatch to the processing plant (100) the particular batch (the amount of chlorine therein being known) that is the most suitable to maintain the maximum flow rate of chlorine through the plant at any given time. In any case, after an initially rejected batch is sent to the plant (100), the controller (500) notes the additional chlorine that is being provided to the plant (100).

A third option (374) is to return the rejected batches of waste in the second channel (364) to the bin (320), to be re-mixed with other waste, and sent through the sorter (200) again.

Any one or all of the above options could be operational at any given time, and the controller (500) may switch from one option to another, according to need. For example, the controller (500) would preferentially use the second option (372) whenever it possibly can; however, if the number of rejected batches reaches a maximum amount that can be sensibly stored and processed, then either the first option (370) or third option (374) may then be selected to deal with the excess. In simpler sorting systems, the second, and even the third options may not be made available, and thus, whenever the level of chlorine in any given batch is above the threshold value, the batch is rejected and disposed of outside of the waste processing plant.

The predetermined threshold can be constant or can vary with time. For example, if the waste being treated is of a substantially homogeneous nature, then an average threshold value can be determined such that will ensure that the level of chlorine being processed by the plant (100) is never too high. The same may also apply for certain types of waste in which the amount of chlorine in the waste is known to be particularly low.

It should be noted that the regulatory limitations refer to the concentration of chlorine containing pollutants that is emitted from the processing plant into the atmosphere. Therefore the threshold level for chlorine in the waste to be admitted into the processing chamber (10) also depends on the efficiency of the air pollution control system (APC), which is installed after the gas outlet (50). A typical APC that is a part of a plasma waste treating plant is capable of removing a significant proportion of the chlorine containing pollutants if it is properly designed and maintained and providing that the concentration of chlorine containing pollutants in the effluent gases is not too high. In other words the higher the efficiency of the APC the higher the threshold value that can be used at the inlet of the processing chamber.

Alternatively, and preferably, the controller (500) is programmed to continually update the amount of chlorine that is currently being processed by the plant (100), and to determine the maximum amount of chlorine that may be permitted in the next batch such that, by the time this batch is introduced into the plant (100), the amount of chlorine being processed thereby is still below the acceptable level. A new temporary threshold value is thus calculated, and the current batch permitted if the level of chlorine is less than this threshold. If not, then this batch is rejected and the controller searches for a suitable batch from amongst those previously rejected and stored according to the second option described hereinabove. In any case, either after introducing a new batch into the plant or waiting a predetermined interval of time if no suitable batch is found, the controller recalculates the amount of chlorine that will be present in the plant (100), and determines on the basis of this calculation what the threshold value for the next batch needs to be. Thus, the threshold value is continually updated such as to maintain the average amount of chlorine in the plant (100) within acceptable values while allowing the maximum rate of processing of chlorine containing waste.

In other embodiments of the system according to the present invention, the sorter (200) may sort the waste into a plurality of channels, according to predetermined criteria. Typically, the predetermined criteria comprise a corresponding plurality of chlorine content ranges, such that the waste is sorted to a channel that corresponds to a particular range. Such embodiments are particularly useful where a plurality of processing chambers (10) are being supplied via one or more such sorters, wherein each sorter can send a particular batch of waste to the most appropriate chamber such as to optimize the amount of chlorine being processed by each of the chambers.

The present invention is also directed to a sorter, which is novel per se for sorting waste material into one of at least two channels according to the level of chlorine therein. In a preferred embodiment, the sorter (200) measures a predetermined quantity of waste (herein referred to as a "batch"), determines the amount of chlorine therein, and according to whether this amount of chlorine compares with predetermined criteria, typically whether it is below or greater than a predetermined threshold value, diverts the batch of waste to a first channel (362) or to a second channel (364), respectively. In other embodiments of the invention, the sorter may be configured to sort the waste into any one of a plurality of channels, each channel corresponding to a range of chlorine concentrations.

Figure 3:
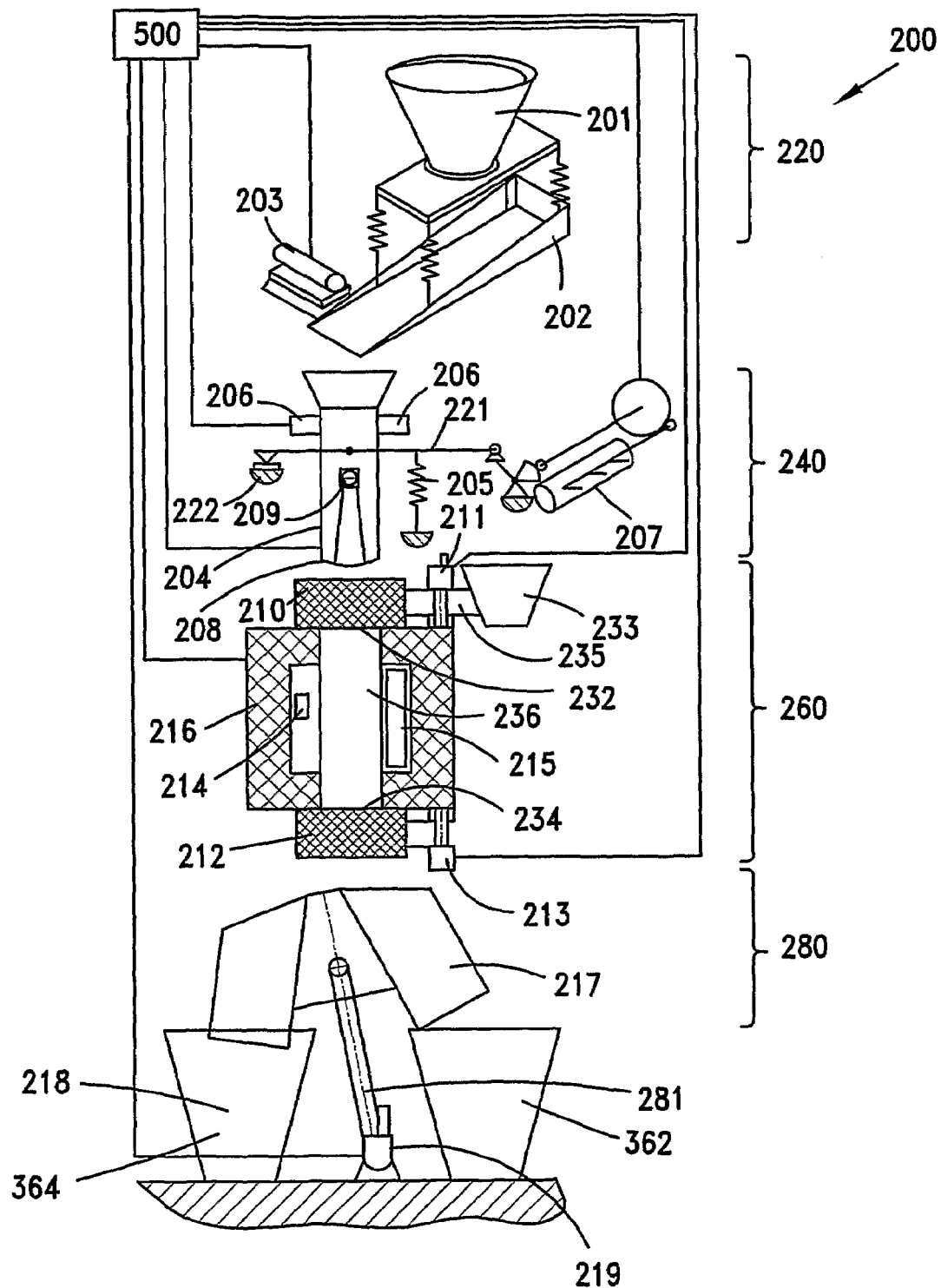
FIG. 3 shows schematically a preferred embodiment of the apparatus of the present invention.

Thus, referring to FIG. 3, a preferred embodiment of the sorter (200) comprises a loading unit (220), a weighing unit (240), a detector module (260) and a diverter gate (280).

The loading unit (220) comprises a hopper (201) or other arrangement for receiving waste from transport system (325), which channels this waste to a vibration table (202). The vibration table (202) is inclined away from the hopper (201) and mounted on springs, and connected to a suitable vibrator (203). As the table (202) vibrates under the action of the vibrator (203), waste at the higher end closest to the hopper (201) migrates towards the lower, open end of the table, eventually falling off the table (202) and into the weighing unit (240). The slope of the table (202) is such that waste only falls from it when the table (202) is vibrated, but generally not otherwise. The vibrator (203) is operatively connected to a control unit, typically the control unit (500) of the system (300), but may be a separate control unit instead. The control unit is adapted for controlling the operation of the vibrator (203), as will be described further herein.

The weighing unit (240) is adapted for receiving a predetermined amount of waste, herein referred to as a "batch", from the loading unit (220); for weighing this batch of waste; and for subsequently delivering this batch to the detector module (260). The weighing unit (240) comprises a container (204) having an open upper end, adapted for receiving waste from the loading unit (220), and a bottom end, which can be selectively closed or opened by means of door (208). The container (204) comprises a suitable level detector (206), for example a microwave level indicator, for determining when the waste in the container (204) has reached a predetermined level, and thus predetermined volume. Detector (206) is operatively connected to the controller (500) and sends an appropriate signal thereto when the waste entering container (204) reaches a predetermined level. In turn, the controller (500) then sends a suitable signal to the vibrator (203) to cease vibrating and thus no further waste is introduced into the container (204). The weighing unit (240) then weighs the amount of waste in container (204).

The weighing may be done in a number of ways. For example, and as illustrated in FIG. 3, the container (204) is pivotally mounted to a lever arrangement (221), one end of which is pivoted with respect to an anchor point (222), and which is balanced by means of a spring (205) or the like, which is compressed or stretched in a predictable manner according to the weight of the container (204). The lever arrangement (221), and/or the spring (205), is connected to a suitable weight determination means (207), which determines the weight of the contents of the container (204) based on the displacement of the lever arrangement (221) or on the deformation of the spring (205). The weight determination means (207) is operatively connected to the controller (500) and sends a signal thereto correlated to the weight of the contents of the container (204). Alternatively, the container (204) may be connected to suitable strain gauges, which measure the weight of the container, and send a suitable signal to the controller (500) representative of the container's weight. Knowing the volume of each batch and its weight, the density of each batch is determined and stored in the controller for later use. At this point, the controller (500) sends a signal to the door (208) causing this to open, typically by means of a powered actuator (209), and thus allow the batch of waste to proceed to the detector module (260). When the container (204) has emptied its contents, the controller (500) sends a signal to close the door (208), and then another signal to the loading unit to continue providing waste to the container (204) until it is again filled.

As described hereinabove, the waste is separated into batches of substantially equal volume, which are then weighed by a suitable weighing unit, which then delivers the weighed batch to the detector module (260). Alternatively, the waste the waste may be sorted into batches of substantially equal weight. The weighing process is repeated, batch after batch, so long as there is waste to be processed.

The detector module (260) uses a neutron activation analysis technique for determining the percentage of chlorine (by weight) in the batch of waste that is delivered thereto. The detector module (260) comprises a neutron moderator casing (216), made from a suitable hydrogenous material. A suitable hydrogenous material is one that is enriched with chemical elements so that it is capable of capturing thermal neutrons with high cross section-probability without emitting gamma-quanta of high energies. An example of such a material is borated polyethylene. The casing (216) has an upper opening (232) and a lower opening (234) thereof, allowing passage of material through the casing (216), via an inner chamber (236). Doors (210), (212), typically made of a material similar to that of the casing (216), enable the upper opening (232) and the lower opening (234), respectively, to be selectively opened or sealed. The doors are activated by means of suitable powered actuators (211), (213), respectively, operatively connected to the controller (500). In one embodiment, door (210) is preferably mounted on one end of an arm (235) having a funnel (233) mounted on its other end.

With this arrangement, rotation of the arm (235) by means of actuator (211) alternately either seals opening (232) or places funnel (233) in position to assist in passage of the batches of waste from weighing unit (240) into inner chamber (236).

A suitable neutron generator (214), for example a portable D-T pulsed neutron generator, is provided in the casing (216). Under typical operating conditions of the detector module (260), the pulsed neutron generator irradiates a batch of waste in the chamber (236) with neutrons of energy of 2.5 Mev or 14.0 Mev for a period of time on the order of several seconds. The emitted neutrons interact with different nuclei within the waste thus producing excited nuclei, which decay emitting gamma quanta of different energies that are characteristic of the nuclei. A suitable spectrometric gamma detector (215), such as for example a NaI(Tl) or a CsI(Tl) scintillation detector, is provided for detecting the gamma quanta emitted by the nuclei in the waste and measuring their intensity as a function of their energy. Specific energies in the obtained spectra are correlated to the interaction of the neutrons with the chlorine nuclei. Using known techniques, the relative amounts of chlorine (by weight) in the batch of waste can be determined from the intensity of the energy spectra at these energies.

Figure 4:
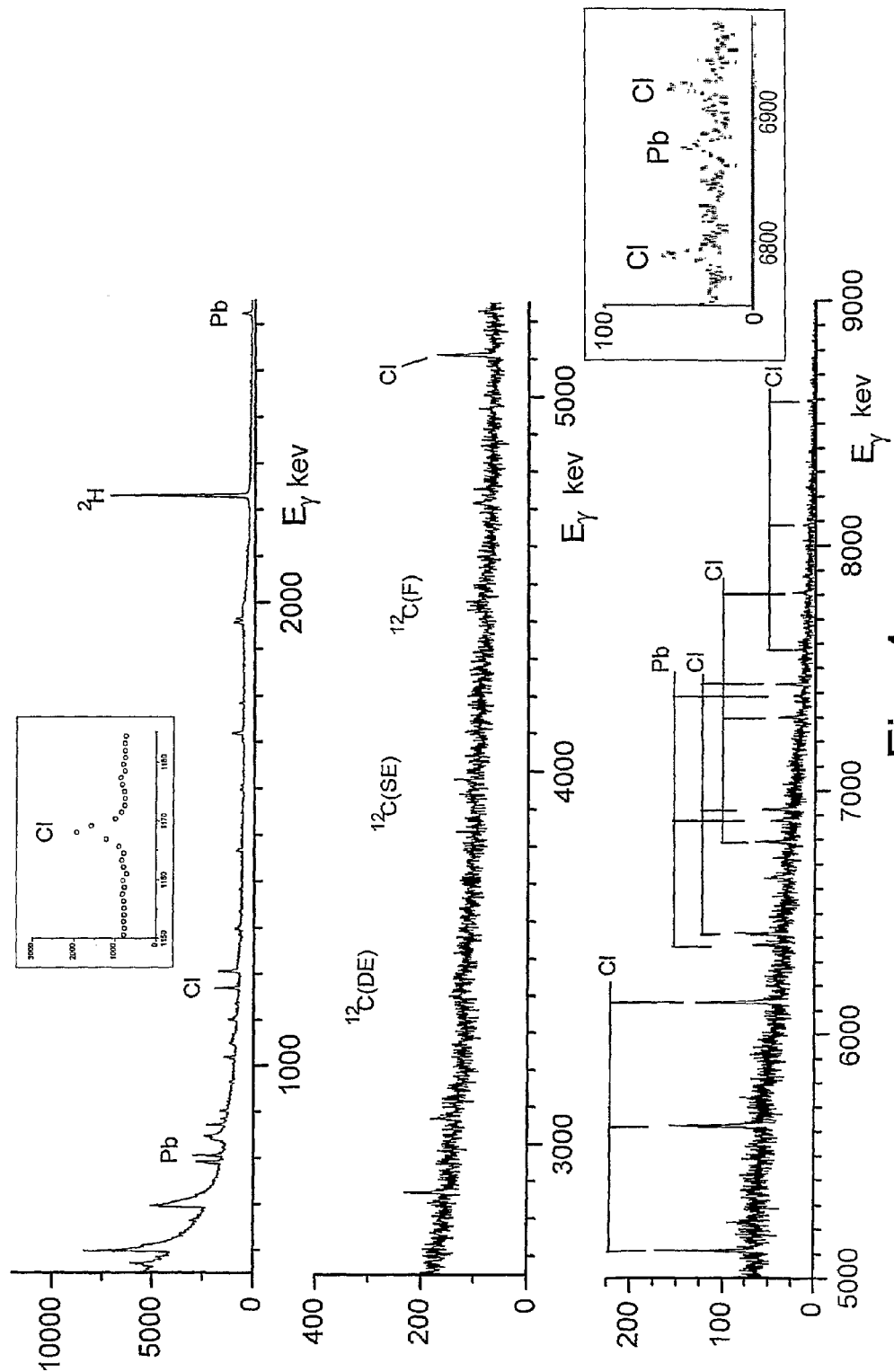
FIG. 4 shows a typical spectrum showing the gamma response of waste material containing 1% chlorine.

FIG. 4 shows a typical spectrum showing the gamma response of waste material containing 1% chlorine. The vertical axis shows the intensity of the emission measured in gamma counts of the detector and the horizontal axis represents the energy of the gamma particles measured in Kev. The nuclei responsible for the prominent peaks are marked on the spectrum and it can be seen that there are several peaks associated with the chlorine nucleus that are suitable for the purposes of this invention.

Preferably, the chamber (236) is substantially cylindrical and smooth, to facilitate passage of the waste therethrough. Optionally, a piston or the like (not shown), conveyor means, or indeed any suitable means, including or excluding gravity, for example air pressure, may be used to urge the waste through the chamber (236). In other embodiments, the detector module (260) may be adapted for receiving and dispensing the batches of waste in a horizontal or inclined orientation rather than vertical, and any suitable transport system may be used for transporting the waste to and from the detector module. For example, a horizontal tube chain conveyor can be used to transport batches of waste through the detector module (260). Such a conveyor can also be designed in an inclined configuration if necessary.

Operation of the detector module (240) is as follows. When the weighing unit is ready to provide a batch of waste to the detector module (260), the controller (500) ensures that the chamber (236) has been emptied of its previous contents (perhaps by opening the lower door (212) for a preset amount of time, and then closing the same; additionally or alternatively a suitable sensor, for example a level sensor, may be provided), and then ensures that the lower door (212) is closed. The upper door (232) is now opened and this is followed by actuation of the door (208) to enable the waste to pass from the weighing unit (240) to the chamber (236) of the detector module (260). Where appropriate, a piston, conveyor belt or other means may be used to transport the waste from the weighing unit (240) to the detector module (260). Then, the upper door (232) is closed, and the controller (500) sends an appropriate command to the neutron source to generate the required neutron emission for a predetermined period of time, typically around 10 seconds and the energy spectrum detected by the gamma detector (215) is relayed to the controller (500). Since the weight of each batch and its volume are known, the controller (500) is able to calculate the density of the waste. From the density and the intensity of the gamma radiation the amount of chlorine (by weight) in the batch is determined.

After the amount of chlorine in the batch is determined, the diverter gate (280) is activated to divert the batch of waste to either the first channel (362) or the second channel (364), according to commands from the controller (500). In the embodiment illustrated in FIG. 3, the diverter gate comprises an assembly of two chutes (217), arranged about a central support (281) that is pivoted to swing between two angular positions. In the first angular position, one of the chutes (217) is immediately below the lower door (212), and is able to divert the waste from the detector module (260) to the first channel (362), while in the second angular position, the other chute (217) is positioned below the door (212) and is thus able to divert the waste to the second channel (364). Powered actuation means (219), operatively connected to the controller (500), swing the diverter gate (280) between the angular positions, according to the determination by the controller as to whether the batch of waste should be diverted to the first channel (362) or second channel (364). Suitable containers (218) or other arrangements may be provided in the first channel (362) or second channel (364) for storing and handling one or more batches of waste at any given time.

While the foregoing description describes in detail only a few specific embodiments of the invention, it will be understood by those skilled in the art that the invention is not limited thereto and that other variations in form and details may be possible without departing from the scope of the invention herein disclosed. For example, the method and apparatus of the invention can be used to determine the amount of other potentially polluting elements in waste and can be used to qualitatively and quantitatively determine the presence of specific elements in other bulk materials, such as coal.

The invention claimed is:

1. An apparatus for the on-line sorting of waste according to its chemical composition and directing said waste into one of two or more channels according to predetermined criterion prior to the introduction of said waste into a waste processing plant or apparatus, wherein said apparatus comprises:
   a loading unit, adapted to accept said waste from one or more external sources;
   a weighing unit, adapted for accepting said waste from said loading unit in batches and determining the weight of each of said batches;
   a detector module, adapted for accepting one of said batches from said weighing unit and determining the presence and amount of one or more specified chemical elements in said batch;
   a diverter gate, adapted to accept said batch of material from said detector module and to direct said batch into one of said two or more channels; and
   a controller, adapted to control the activation and the timing of the activation of the elements of said apparatus and to perform calculations and store data necessary for the operation of said apparatus;
   characterized in that: said waste is not presorted prior to entering said loading unit; said detector module comprises elements for performing a neutron activation analysis technique to determine the presence and amount of said one or more specified chemical elements in said batch; that the results of said determination is used to decide into which of said channels said batch is to be directed; and said predetermined criteria, is whether the amount of said specified chemical is less than or greater than a predetermined threshold value; wherein said detector module comprises:
   a neutron moderator casing, made from a suitable hydrogenous material, said casing having an upper and a lower opening that can be selectively opened or sealed by doors;
   an inner chamber whose shape and dimensions are defined by the inner walls of said casing and said upper and lower openings;
   a suitable neutron generator for emitting neutrons to irradiate a batch of waste in said inner chamber; and
   a suitable spectrometric gamma detector for detecting gamma quanta;
   wherein, said emitted neutrons interact with different nuclei within said material thus producing excited nuclei, said excited nuclei decay emitting gamma quanta of different energies that are characteristic of said nuclei, and said detector detects said gamma quanta emitted by said nuclei and measures their intensity as a function of their energy.

2. An apparatus according to claim 1, wherein the specified chemical element is chlorine.

3. An apparatus according to claim 1, wherein the suitable hydrogenous material is borated polyethylene.

4. An apparatus according to claim 1, the upper door is pivotally mounted on one end of an arm which has a funnel mounted on its other end, such that, upon rotation of said arm, alternately said upper door either seals the upper opening or said funnel is moved into position to assist in passage of the batches of waste from the weighing unit into said inner chamber.

5. An apparatus according to claim 1, wherein the neutron generator is a portable D-T pulsed neutron generator.

6. An apparatus according to claim 1, wherein the energy of the emitted neutrons is 2.5 Mev.

7. An apparatus according to claim 1, wherein the energy of the emitted neutrons is 14.0 Mev.

8. An apparatus according to claim 5, wherein the period of time of the pulses are on the order of several seconds.

9. An apparatus according to claim 8, wherein the pulses are emitted for a period of time on the order of 10 seconds.

10. An apparatus according to claim 1, wherein the spectrometric gamma detector is chosen from the group comprising: NaI(Tl) and CsI(Tl)-scintillation detectors.

11. A system for processing waste, said system comprising the sorting apparatus of claim 1 and further comprising:
   a waste processing plant or apparatus;
   a waste receiving bin, into which waste from a plurality of sources is initially dumped, awaiting transport to said sorting apparatus and eventual processing by a waste processing plant or apparatus; and
   a suitable transport system for transporting waste from said bin to said sorting apparatus and from said sorting apparatus to said waste processing plant or apparatus or to some other location;
   wherein said sorting apparatus has three functions: the first function being to divide said waste into substantially equal-volume batches, the second function being to measure the amount of chlorine present in each of said batches, and the third function being to feed each of said batches of waste into one of two channels according to said measured amount of chlorine and use of said system insures that the amount of chlorine containing compounds introduced into said plant or apparatus for the conversion of waste does not exceed a predetermined value; wherein, if the amount of chlorine present in a batch is above a predetermined threshold, said batch is rejected and diverted to the second of the two channels, to be disposed of in a manner selected from the group comprising the following options:
   option 1, the rejected batches of waste, in said second channel, are stored, and eventually disposed of by not being admitted to said waste processing plant or apparatus;
   option 2, the rejected batches of waste, in said second channel, are placed in temporary storage, and dealt with at a later time; and
   option 3, the rejected batches of waste in said second channel are returned to said bin, to be remixed with other waste, and sent through said sorting apparatus again.

12. A system according to claim 11, wherein, if the amount of chlorine in a batch is below a predetermined threshold, the batch is accepted and diverted to the first of the two channels; wherein said batch of waste is transported to the processing plant, to be processed therein in the normal manner.

13. A system according to claim 11, wherein the rejected batches of waste, according to option 1, are disposed of at specially designated sites such as municipal solid waste landfills.

14. A system according to claim 11, wherein each of the rejected batches of waste, according to option 2, is assigned an identification numbed by the control unit, which also contains data regarding the amount of chlorine in each of said batches and the flow rate of waste through the processing plant; whereby, at any given time, the amount of chlorine present in the waste that is being processed by said processing plant is known; additionally suitable sensors at the gas outlet of said plant monitor the gaseous chlorine compounds emitted by said plant and provide this data on a real time basis to said controller; whereby, said controller can then determine whether at any given time, the level of chlorine containing emission is sufficiently low to permit one or more of said rejected batches in the second channel to be introduced into said plant.

15. A system according to claim 14, wherein the rejected batches of waste, according to option 2, are further sorted or arranged on a turntable type arrangement such that the controller can select, access, and dispatch to the processing plant the particular batch that is the most suitable to maintain the maximum flow rate of chlorine through said plant at any given time.

16. A system according to claim 11, wherein any one or all of the options 1 to 3 are operational at any given time, and the controller may switch from one option to another, according to need.

17. A system for processing waste, said system comprising apparatus for the on-line sorting of waste according to its chemical composition and directing said waste into one of two or more channels according to predetermined criterion prior to the introduction of said waste into a waste processing plant or apparatus, wherein said apparatus comprises:
   a loading unit, adapted to accept said waste from one or more external sources;
   a weighing unit, adopted for accepting said waste from said loading unit in batches and determining the weight of each of said batches;
   a detector module, adapted for accepting one of said batches from said weighing unit and determining he presence and amount of one of more specified chemical elements in said batch;
   diverter gate, adapted to accept said batch of material from said detector module and to direct said batch into one of said two or more channels: and
   a controller, adapted to control the activation and the timing of the activation of the elements of said apparatus and to perform calculations and store data necessary for the operation of said apparatus;
   wherein: said waste is not presorted prior to entering said loading unit; said detector module comprises elements for performing a neutron activation analysis technique to determine the presence and amount of said one or more specified chemical elements in sad batch; that the results of said determination is used to decide into which of said channels said batch is to be directed; and said predetermined criteria, is whether the amount of said specified chemical less than or greater than a predetermined threshold value, said system further comprising:
   a waste processing plant or apparatus;
   a waste receiving bin into which waste from a plurality of sources is initially dumped, awaiting transport to said sorting apparatus and eventual processing by a waste processing plant or apparatus; and
   a suitable transport system for transporting waste from said bin to said sorting apparatus and from said sorting apparatus to said waste processing plant or apparatus or to some other location;
   wherein said sorting apparatus has three functions: the first function being to divide said waste into substantially equal-volume batches, the second function being to measure the mount of chlorine present in each of said batches of the third function being to feed each of said batches of waste into one of two channels according to said measured mount of chlorine and use of said system insures that the amount of chlorine containing compounds introduced into said plant or apparatus for the conversion of waste does not exceed a predetermined value, wherein the waste processing plant or apparatus process the waste by using a thermal treatment process.

18. A system according to claim 17, wherein the thermal treatment process comprises the use of one or more plasma torches.

19. A method for operating the system of claim 11 comprising the steps of:
- dumping waste from a plurality of sources into the waste receiving bin;
- transporting at least part of said waste from said waste receiving bin to the loading unit of the sorting apparatus;
- loading at least part of said transported waste into said loading unit;
- transferring at least part of said waste in said loading unit to the weighing unit;
- stopping transfer of waste into said weighing unit when a predetermined amount of waste, thus forming a batch of waste, has entered said weighing unit;
- transferring said batch of waste to the detector module;
- sealing the doors of said detector module;
- activating the neutron generator to irradiate said batch of waste in said detector module, thus creating excited nuclei in at least some of the molecules of the material of which said batch of waste is comprised;
- activating the gamma detector to measure the quantity and energy of the gamma quanta emitted by said excited nuclei;
- directing said batch through a diverter gate to one of two or more channels; and
- repeating all of the above steps until no more waste remains in said receiving bin or the processing of said waste must be suspended for some other reason;
- wherein, the selection of which one of said two or more channels to which said batch is directed is dependent on the results of said measurement of the quantity and energy of said gamma quanta and one of said channels leads directly to the waste processing chamber of the waste processing plant or apparatus and a second of said two or more channels leads to either a temporary storage area, back to said waste receiving bin, or to a disposal area that is not a part of said waste processing plant or apparatus.

20. A method according to claim 19, wherein a controller is used to control the execution and the timing of the steps of said method and to perform calculations and store data necessary for carrying out said method.

* * * * *